United States Patent [19]

Klein

[11] Patent Number: 4,527,554

[45] Date of Patent: Jul. 9, 1985

[54] METHOD AND DEVICE FOR MAKING A TWISTED WIRE CONNECTION WITH REDUCED INCIDENCE OF BREAKAGE

[76] Inventor: Harvey A. Klein, 1000 E. 19th St., Brooklyn, N.Y. 11230

[21] Appl. No.: 416,900

[22] Filed: Sep. 13, 1982

[51] Int. Cl.³ ............................................. A61F 5/04
[52] U.S. Cl. ............................... 128/92 B; 128/92 E; 623/16
[58] Field of Search ....................... 3/1, 1.9; 128/92 R, 128/92 B, 92 E; 140/93.6, 96 A

[56] References Cited

U.S. PATENT DOCUMENTS 1,463,869 8/1923 Campbell ............................ 140/93 A
3,273,605 9/1966 Ferrara, Jr. ......................... 140/93.6

FOREIGN PATENT DOCUMENTS 868045 2/1953 Fed. Rep. of Germany .... 128/92 B
0594973 1/1978 U.S.S.R. ............................. 128/92 B Primary Examiner—Richard J. Apley
Assistant Examiner—David J. Isabella
Attorney, Agent, or Firm—Israel Nissenbaum

[57] ABSTRACT

A method for making a twisted wire connection, particularly as utilized in surgical procedures, with reduced incidence of breakage comprising tensioning and twisting such wires without sliding pressure contact against a stationary frictional surface. A rolling surface, movable with the wires, is utilized whereby stress and scoring of the wires is substantially reduced or eliminated. Initial tensioning of the wires is preferably by minor or imperceptible increments to avoid shock wave transmission and degradation of the wires. Twisting of the wires is effected uniformly (with reduced stress concentration) by maintaining a constant axis for the wires during twisting. A device having rolling members, a one way roller clutch, and a stabilized base for effecting such method is also described.

19 Claims, 3 Drawing Figures

METHOD AND DEVICE FOR MAKING A TWISTED WIRE CONNECTION WITH REDUCED INCIDENCE OF BREAKAGE

This invention relates to methods for making tightened wire connections used in holding objects together and wire connection forming devices, with particular applicability in surgical procedures such as in orthopedic surgery wherein broken bones are held together during healing by tightened and twisted wires.

A common procedure in orthopedic surgery, to insure proper knitting of broken or severed bones, is the utilization of holding devices to maintain bone fragments in tight proximity during the six weeks generally required for healing. A common holding device for such purpose is pliable wire such as of surgical stainless steel, marketed, for example, in 18-20 gauge. The wire is utilized by drawing it through holes drilled proximally and distally to the bone fragments, with the ends thereof being externally tightened and twisted into a locking, generally helical tie. The helical tie is then bent and tucked into one of the drilled holes to complete the procedure. It has, however, been determined that about 13% of the wires utilized for such purpose break at the base of the helix while in the body. This amount of wire breakage is in addition to the number of wires which break during surgery and which are immediately replaced but at a cost of time and effort. Breakage of the wires during the early stages of healing may result in a less than ideal knitting of the bone fragments. Breakage at any time even after healing may result in a loose sharp wire end which can easily penetrate into a bursa or muscle belly, causing pain and necessitating surgical removal.

It is an object of the present invention to provide a method for making twisted wire connections having reduced incidence of breakage.

It is a further object of the present invention to provide a device for effecting such method.

It is a still further object of the present invention to provide said method and device for surgical applications, especially in orthopedic surgery wherein wire breakage is of particular concern.

These and other objects, features and advantages of the present invention will become more evident from the following discussion as well as the drawings in which.

Figure 1:
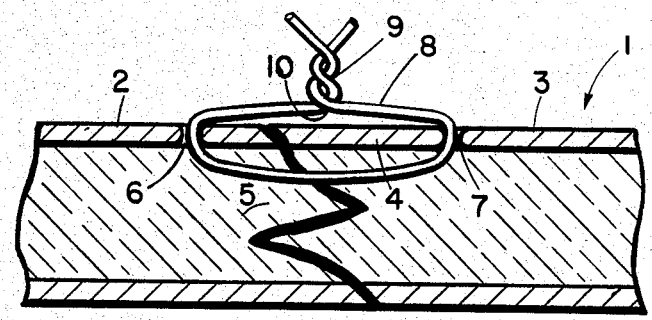
FIG. 1 is a partially sectioned view of bone fragments being held together in healing position by a twisted wire connection.

I have discovered that a major factor contributing to the breakage of the tensioned and twisted wires used in effecting bone fragment connections, is the scoring and localized stressing of such wires at the base of the helical tie, i.e. below the region of contact of the wires with each other, caused by the very tools utilized in making the twisted wire connection. Because of the inherent pliable nature of the connecting wire, whereby it must be capable of being easily twisted into a tie, such wire is particularly prone to breakage caused by such scoring and localized stressing. The present invention therefore generally comprises a method for making a twisted wire connection with substantially reduced scoring and localized stressing and therefore reduced breakage; and a device for effecting said method.

The method of the present invention comprises forming a twisted wire connection while eliminating the sliding contact against a stationary frictional surface inherent in prior art methods and devices used in making twisted wire connections. In such prior art the wires were tensioned and twisted against the stationary surfaces with scoring and stressing of the wires resulting from the sliding relative movement. The required tensioning and twisting of a relatively soft wire against the stationary frictional surface, generally of a metal hard enough to withstand exerted pressures, usually scored, or at the very least, unduly stressed the wire at the point of contact therebetween. As a result, a point of weakness was created in the wire. Furthermore, because of the manner of operation of prior art devices, such point of weakness was generally located at the base of the helix (or wire twist) which point remained in constant tension. Breakage of the wire at that point was therefore not uncommon. Even devices having smooth rather than sharp edged contact surfaces produced wire connections susceptible to breakage, since the contact surfaces still resulted in a scoring or stress producing sliding frictional contact with applied pressure.

In a preferred embodiment of the present invention the stationary frictional contact surface of the prior art is replaced with a surface which moves together with the wire during the tensioning and twisting procedures. A rolling surface provides such movement while also providing a buttressing contact during tensioning and twisting of the wire with resultant very minimal friction between the wire and the rolling surface. Since the surface moves with the wire, the scoring and stressing of the wire is substantially reduced or even eliminated entirely, with wire breakage being concomitantly reduced or eliminated. The method of the present invention therefore comprises the steps of passing a wire in holding juxtaposition, such as through or around the objects to be connected, then tensioning and twisting the wire ends against a rolling surface point or points of contact to make a holding wire connection and to lock it into position. The wire ends do not otherwise contact stationary frictional surfaces, with any exerted pressure, between the base of the tie-twist, i.e. the region at which the wires contact each other, when completed, and the objects to be joined by the twisted wire connection.

In a further preferred embodiment of the present invention, the tensioning of the wire ends is in itself accomplished by the step of very small or imperceptible increments, i.e. with a smooth tensioning motion. This provides an improvement over prior art tensioning methods which utilized, for example, ratchet type mechanisms with relatively large increments in tensioning. At the end of each of the finite incremental stages, a detrimental shock wave was transmitted through the wires, thereby causing highly stressed points to weaken further. Additionally, because of the inability to discontinue tensioning within the incremental stage, prior art tensioning methods also occasionally led to overtensioning with resultant damaging stress on the wires.

In a still further embodiment of the present invention, the wire ends, during twisting, are maintained in a fixed perpendicular axis relationship relative to the objects, such as bone fragments, which are to be held together by the twisted wire tie. As a result, a uniform helix (or twist tie) is formed thus avoiding imperfect twisting and resultant localized stress raisers. Prior art methods of wire twisting entailed the use of generally unsupported hand held devices which tended to toggle or move off the perpendicular axis during twisting of the wire. Such toggling resulted in non-uniform or imperfect twisting with localized points of stress which contributed to wire breakage. If further desired, both the tensioning and twisting procedures of the present invention may be effected to predetermined tensions to maximize the holding power of the twisted wire connection while minimizing stresses which result from overtensioning or overtwisting.

A device for use in effecting the aforementioned method of the present invention, comprises a supporting frame on which is affixed means for providing a movable contact surface such as a rolling contact surface, against which the ends of a wire are buttressed for tensioning, during the formation of a twisted wire conection with the wire moving together with such surface. The supporting frame also embodies means for tensioning said wire ends to ensure positive holding of said wire connection prior to and during locking thereof by twisting of said wire ends together. Preferably tensioning with said tensioning means is imperceptibly incremental. Said supporting frame further embodies means for permitting twisting of the tensioned wire ends, and preferably with means for maintaining said twisting, around a fixed axis or frame of reference. Means for stopping both tensioning and twisting at a predetermined tension and twisting are also preferably embodied with said support frame.

With specific reference to the drawings, FIG. 1 depicts a broken bone 1 with fragments 2 and 3 which are held in proper alignment with surgical wire 8. To effect such connection, apertures 6 and 7 are drilled into adjacent areas of fragments 2 and 3 respectively through the cortex 4 to the relatively hollow medullary canal 5 of the bone 1. Sterile surgical wire 8 is then snaked through one of the apertures 6 or 7 and the medullary canal 5, and then out the other aperture. The ends of wire 8 are then tightened or tensioned to bring the bone fragments 2 and 3 into close abutting relationship for proper healing. The tensioned wire ends are thereafter twisted into helical tie formation 9 to lock the abutting fragments 2 and 3 in the proper healing position. During the procedures of tensioning and twisting the area of the wire ends subject to the greatest degradation, engenedered by tools commonly used to effect such tensioning and twisting, is at the base 10 of helical tie 9 since base 10 is in direct pressure contact with said tools.

Figure 2:
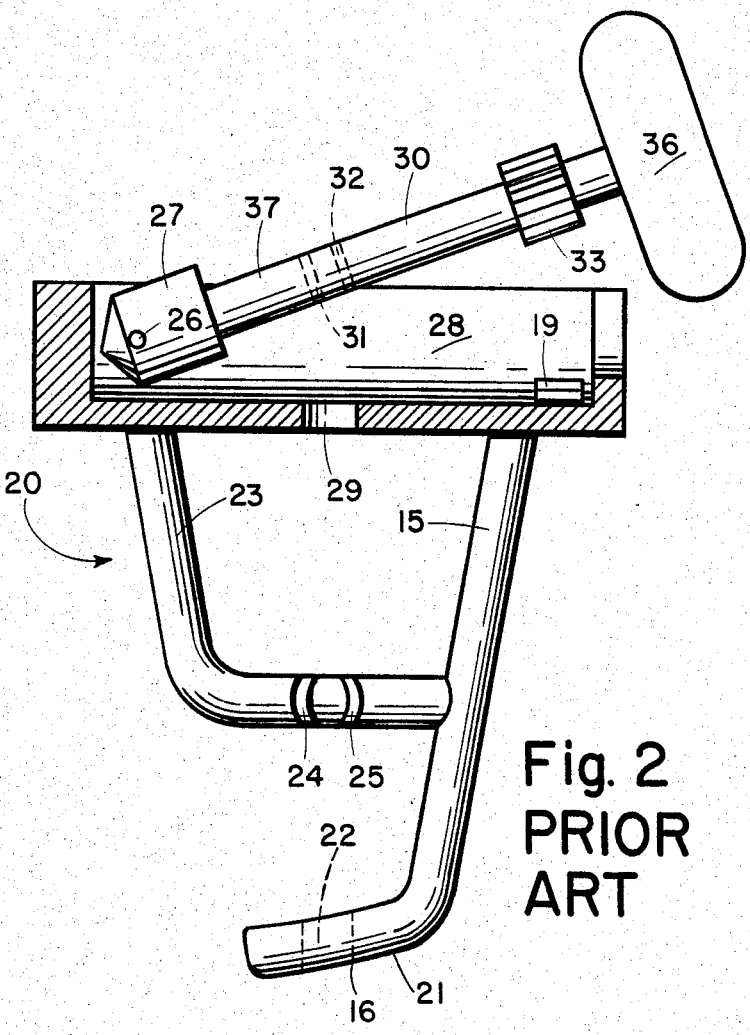
FIG. 2 is a partially sectioned plan view of a prior art wire twisting device commonly utilized in effecting the twisted wire connection shown in FIG. 1.

Exemplary of prior art tools utilized in orthopedic surgery for effecting a twisted wire connection is device 20 shown in FIG. 2, comprised of a figure "9" shaped supporting frame 15 with an aperture 22 in angled base section 21. The wire ends, after being drawn through the bone fragments, are routed through said aperture 22 and are then individually routed through angled guide slots 24 and 25 in cross bar member 23 and into holes 31 and 32 of separable spindle member 30. Said spindle member 30 is then seated into channel 28 in the top segment 29 of supporting frame 15, with the end 37 of spindle member 30 being fitted into swiveling retaining cup 27, held in channel 28 by support pin 26. When spindle member 30 is seated, gear member 33 engages pawl 19 at the base of channel 28 to form a one way ratcheting mechanism. Rotation of lever member 36 on spindle member 30 tensions the wire ends by winding thereof on said spindle and this tension prevents upward motion of the spindle from its seat in channel 28. When the wire ends are sufficiently tensioned, with base section 21 being drawn into contact with the bone, the device 20 is completely manually twisted around a vertical or perpendicular axis relative to the near surface of the bone 1 with such wire ends being twisted thereby into helical tie formation 9 as shown in FIG. 1. The twisted wire is then cut at a point below cross bar member 23 and is then tucked into one of apertures 6 or 7 in bone 1 in order to prevent extended sharp edges.

During both the tensioning and twising procedures just described, lower peripheral edge 16 in aperture 22 is in constant tensioned contact with the wire ends as a buttress for the tensioning and twisting. As a result, the wire at the point of such contact, i.e. the base 10 of helical tie 9 becomes a stress raiser and is seriously deformed with increased susceptibility to breakage. Furthermore, depending upon the number of teeth in gear 33, the tensioning of the wire ends is by finite angular increments (360/no. of teeth) generally about 30°. Each engagement of pawl 19 with the teeth in gear 33 causes a shock wave to be transmitted through the wire ends which further stresses the already weakened wire in contact with edge 16. Additionally, when a proper tension falls within the specific angular increment, the wire ends must be overtensioned with still further stress being placed on the aweakened portion or portions of the wire.

When the wire ends are deemed to be sufficiently tensioned, they are then twisted into a helical tie by rotation of the entire device 20 around its central axis or the axis vertical to or perpendicular to the near surface of the bone. However, because of such rotation of the entire device and the angled position of base section 21, without a fixed frame of reference, maintenance of such twisting along the vertical axis is almost entirely dependent upon the manual dexterity of the operator. Invariably, toggling (or deviations from such axis) occurs with resultant imperfect helical tie formation, localized stressing of the wire and deformation thereof.

Figure 3:
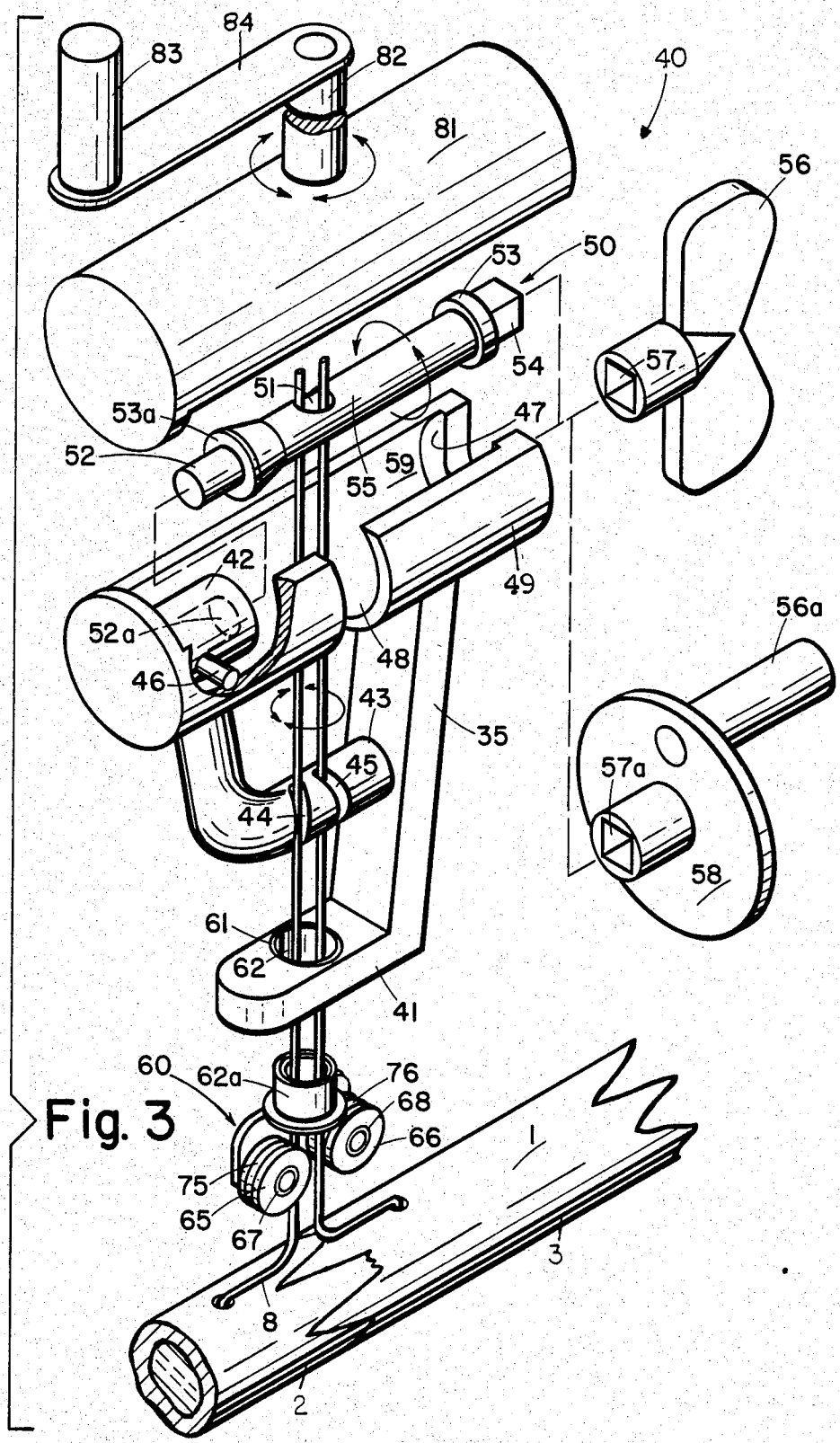
FIG. 3 is a partially sectioned exploded isometric view of the device of the present invention with preferred embodiments thereof.

The wire tightening and twisting device 40 of the present invention shown in FIG. 3 obviates many of the problems inherent in prior art tightening and twisting devices, such as the one shown in FIG. 2 and described above. Wire connection forming device 40 basically comprises a supporting frame 35 having positioned thereon rolling elements or members 65 and 66 in the form of pulleys having rounded grooves 75 and 76 repectively therein with diameters of said grooves being sizes to accommodate the specific wire used in effecting the connection. The pulleys 65 and 66 are affixed to supportive body member 60 therefor, which is in turn affixed to and extends below base section 41 of support frame 35 by means of a bearing surface which allows free rotation of the supportive body member 60 with respect to the support frame 35. The pulleys 65 and 66 are mounted to said body member 60 upon pulley bearings by means of pulley bearing pins, 67 and 68 respectively, whereby said pulleys fixedly rotate about axes parallel to each other. Rotation of the pulleys is in a plane perpendicular to the bone to be connected. With the free rotation of body member 60, the parallel axes of said pulleys are in a plane parallel to the near surface of the bone. Supportive body member 60 is rotatably held within aperture 62 of base section 41 by means of a bearing 61 adjacently situated about the periphery of said aperture, whereby said supportive body member 60 and the frame 35 are mutually rotatable around an axis perpendicular to the near surface of the bone. Rotating body member 60 is in turn internally apertured along said perpendicular axis and provides an opening which permits wire ends to be passed therethrough along said perpendicular axis. Body member 60 is thereby circumferentially rotatable around said wire ends.

Pulleys 65 and 66 are closely adjacent one another in a longitudinal plane preferably at a distance between the bases of grooves 75 and 76 of less than the diameter of aperture 62a in body member 60 in order to insure that wires drawn therebetween and through aperture 62a do not contact the walls thereof. During the initial formation of the wire connection, the ends of wire 8, having already been drawn through the bone fragments 2 and 3, are further drawn between pulleys 65 and 66 and seated into grooves 75 and 76 respectively which are sized to accommodate such wire ends. (Body member 60 may be removably held by support frame 35 such as by a "C" clip whereby pulleys having grooves of varying diameters may be substituted to accommodate different size wires.) The wires are then drawn through aperture 62a of body member 60 and routing angled slots 44 and 45 in cross bar member 43 (said slots being preferably spaced at a distance from ach other less than the diameter of aperture 62a to insure lack of contact with the walls of said aperture) into aperture 51 of spindle member 50 in a manner similar to that described with respect to prior art spindle 30 shown in FIG. 2. However, spindle member 50 of the present invention is comprised of a shaft 55 with an end 52 thereof of hardened or case hardened metal (preferably of at least Rockwell-C 58-60) which is seated within a one way roller clutch 52a which is in turn stationarily seated within swiveling roller clutch housing 42 held by clutch housing pin 46 in channel 48 of frame top segment 59. Said top segment 59 is positioned substantially parallel to base section 41. Spindle member 50 is then seated within channel 48 with spindle extension member 53 engaging keyed channel member 47 thereby preventing lateral movement of spindle member 50. Similarly, stop 53a prevents full insertion of end 52 into the roller clutch mechanism. Lever member 56, keyed to fit distal end 54 of spindle member 50, is connected thereto and then said spindle is wound therewith in the direction permitted by the one way roller clutch (clockwise in the configuration shown). Lever member 56 may be integrated with spindle member 50 or more preferably may be replaced by slip clutch drive member 58 which may be adjusted to slip at a preselected tension.

With the rotation of the spindle member 50, the wire ends are wound therearound and tensioned against a buttressing force exerted by pulleys 65 and 66. However, in contrast to the prior art, said pulleys move together with the wire and ride down the wire ends with only rolling frictional contact between said pulleys and the wire ends. With continued tensioning, the pulleys are brought into firm contact with the near surface of the bone with the parallel positioning of base section 41 with said bone surface facilitating said firm contact. In order to further reduce any frictional drag, the pulley bearings may be coated with frictional reducing materials such as polytetrafluoroethylene (PTFE).

When a proper or preselected tension is attained, body member 60 and pulley members 65 and 66, in conjunction with the tensioned wire 8 therebetween are fixed into position on bone 1 and thereby provide a stationary base or frame of reference for the wire twisting device 40. Frame 35 and base section 41 are then rotated, without toggling or significant deviation from the perpendicular or vertical axis of rotation, around fixed position body member 60 with tensioned wire ends to form an essentially perfect helical tie 9. Bearing 61 may be coated with PTFE to facilitate such rotation.

Rotation of frame 35 may be simply manually effected, or more preferably, a rotator housing 81 with rotatable sleeve 82, aligned with the perpendicular axis along which the wire ends are twisted, is slipped over external housing 49 of channel 48. Within said sleeve 82 (not shown) lever member 84 has an extension thereof keyed to and fitted to an integral extension of rotator housing 81 whereby rotation of floating handle 83 twists or cranks said housing and concomitantly said frame 35. Alternatively, as with the tensioning operation, a slip clutch drive lever may be affixed to said extension of rotator housing 81. During the twisting operation, sleeve 82 is manually held in position and the slip clutch drive lever is rotated with concomitant cranking or winding rotation of frame 35 and the wire ends to form the requisite locking helical tie. At the predetermined twisting or twisting tension or at the option of the operator, the twisted wire connection is completed. The twisted wire is then cut below cross bar member 43 aand tucked into one of apertures 6 or 7 in said bone. Wire tie connections made with the device and in accordance with the method of the present invention display no scoring of the wire ends and are markedly less susceptible to wire breakage.

The method and device of the present invention have particular applicability in various types of surgery including hip surgery, closure of the sternum following open heart surgery, some types of elbow surgery and the like.

It is understood, however, that the above description and the drawings are illustrative in nature and that changes may be made such as with respect to the structure and configuration of the device and its application, and that similar changes may be effected in implementing the method of the present invention without departing from the scope of the present invention as defined in the following claims.

What is claimed is:

1. A method for making a twisted wire connection for holding objects together, with reduced incidence of breakage comprising the steps of;
   (a) positioning a wire in holding juxtaposition with objects to be held together with said wire;
   (b) tensioning the ends of said wire against buttressing means after said wire is positioned, whereby said wire holds said objects together; and
   (c) twisting said tensioned wire ends into a tie whereby said wire connection is locked into a position for holding said objects together;
   wherein said method comprises the steps of establishing a fixed axis, perpendicular to said objects being held together, along which axis said wire ends extend; tensioning said wire ends against at least one rolling element which moves together with said wire ends during tensioning, and wherein said wire ends and at least one of said rolling elements move in the same direction away from said objects and along said fixed axis during tensioning; whereby scoring or stressing of said wire ends, with resultant wire breakage, is substantially reduced or eliminated, and thereafter twisting said wire ends around said fixed axis.

2. The method of claim 1 wherein said step of tensioning the wire ends is by imperceptible increments.

3. The method of claim 2 wherein said tensioning is automatically stopped at a predetermined tension.

4. The method of claim 1 wherein said twisting is automatically stopped at a predetermined twisting tension.

5. The method of claims 1, 2, 3, or 4 wherein said objects comprise bone fragments.

6. A method for making a twisted wire connection for holding bone fragments together during healing with reduced incidence of breakage, comprising the steps of passing a wire through at least one aperture in each of said bone fragments, with the ends of said wire being external to said bond fragments, and tensioning and twisting said wire ends together to form said twisted wire connection, wherein said method comprises the steps of tensioning and twisting of said wire ends while maintaining the region of said wire ends, between said bone fragments and the point of contact of said wire ends with each other, out of pressure contact with any stationary frictional surface, wherein said wire ends are each tensioned to a substantially equal extent against one of two rotating pulleys, and wherein said tensioned wires are held along a fixed axis perpendicular to said bone fragments aroud which said wires are twisted.

7. The method of claim 6 wherein said region of said wire ends is buttressed against a rolling surface which moves with said wire ends during said tensioning and twisting.

8. A device for making a twisted wire connection for holding objects together comprised of a supporting frame having means for establishing a fixed axis perpendicular to said objects being held together along which axis the ends of said wire are tensioned and twisted, wire tensioning means, means for buttressing said wire during said tensioning, and wire twisting means, wherein said buttressing means comprises two rotating pulleys being closely adjacent one another in a longitudinal plane and having fixed parallel axes of rotation relative to one another, wherein said tensioning means causes said wire ends to be tensioned together along said perpendicular axis in the same direction which is away from said objects, and wherein the direction of rotation of said pulleys during said tensioning coincides with the direction of tensioning of said wire ends.

9. The device of claim 8 wherein said supporting frame further embodies means for tensioning said wire ends against said buttressing means by substantially imperceptible increments.

10. The device of claim 8 wherein said grooved pulleys are circumferentially grooved with the diameter of the grooves therein being sized to accommodate said wire therein tensioning of said wire ends closely adjacent one another in a longitudinal plane and having fixed parallel axes of rotation relative to one another, with the direction of rotation of said pulleys being adapted to coincide with the direction of tensioning of said wire ends.

11. The device of claim 10 wherein said grooved pulleys are rotatably affixed to an apertured portion of said supporting frame with said fixed perpendicular axis extending between said pulleys and through said apertures, with said pulleys and said supporting frame being adapted to be rotatable relative to each other in a direction circumferential to said fixed perpendicular axis.

12. The device of claim 9 wherein said tensioning means comprises a one way roller clutch affixed to said supporting frame, wherein a rotating spindle member having wire holding means thereon is engagable with said one way roller clutch for effecting said tensioning of the wire ends by rotation of said spindle member.

13. The device of claim 12 wherein said rotating spindle member has affixed thereto a slip clutch drive member for tensioning of said wire ends, by rotation of said spindle member to a predetermined tension.

14. The device of claim 8 wherein said means for providing a substantially fixed axis for twisting said tensioned wires therearound comprises a base member rotatably affixed to said supporting frame whereby said supporting frame and base member are adapted to be rotatable relative to each other in a direction circumferential to said tensioned wire ends and wherein after tensioning of said wires, said base member is adapted to be substantially fixed into position on said objects, thereby defining said fixed axis for twisting of said wire ends.

15. The device of claim 14 wherein said pulley members are further adapted to be substantially fixed into stationary position on said objects, with said body member being fixed thereby into stationary position on said objects thereby defining said fixed perpendicular axis for twisting of said wire ends.

16. The device of claim 14 wherein said supporting frame further supports a fixed extension member thereof longitudinally aligned with said fixed axis, wherein a floating sleeve is positioned around said extension member and a lever member is attached to said extension member whereby twisting of said lever member, while said sleeve is held in position, turns said extension member and said supporting frame in effecting said twisting of said wire ends together.

17. The device of claim 16 wherein said lever member comprises a slip clutch drive set to slip at a predetermined twisting tension.

18. A device for making a twisted wire connection, for holding bond fragments together during healing, comprising a supporting frame having two spaced, substantially parallel members thereof adapted to be aligned in parallel with said bone fragments during operation of said device, wherein the first of said parallel members, adapted to be adjacent said bone fragments during operation of said device, is apertured along an axis mutually perpendicular to said parallel members and said bone fragments, said aperture having a bearing situated about the internal periphery thereof, with said bearing rotatably supporting a body member having an opening fixedly coincidental with said aperture, said body member being adapted to extend between said first parallel member and said bone fragments with said body member having two grooved pulleys rotatably mounted thereon pulley bearings, said pulleys being adjacent one another in a longitudinal plane and rotatable in a direction along said perpendicular axis with the grooves of said pulleys being adapted to accommodate said wire, said pulleys being situated on said body member such that wire and drawn along said perpendicular axis, pass through the opening in said body member without contacting either of said body member and said first parallel member, said pulleys being further adapted to be fixedly seated on said bone fragments to provide a fixed frame of reference to said perpendicular axis, with said supporting frame being freely rotatable around said body member on said bearing, and wherein the second of said parallel members embodies a channel therein having a one way roller clutch affixed therewithin such that a spindle member, having wire holding means thereon, may be seated within said channel into engagement with said one way roller clutch whereby rotation of said spindle is along an axis situated in a plane parallel to said bone fragments.

19. The device of claim 1 wherein said apertured portion of said supporting frame and said pulleys are rotatably affixed to each other by means of bearing surfaces.

* * * * *